United States Patent [19]
King

[11] Patent Number: 5,429,390
[45] Date of Patent: Jul. 4, 1995

[54] VACCINATION SCHEDULER

[76] Inventor: Dannie H. King, P.O. Box 5005, Rancho Santa Fe, Calif. 92067

[21] Appl. No.: 328,784

[22] Filed: Oct. 28, 1994

[51] Int. Cl.⁶ .............................................. B42D 15/00
[52] U.S. Cl. ...................................... 283/65; 283/115
[58] Field of Search .................... 283/65, 66.1, 66.2, 283/115, 900, 901, 117; 281/51

[56] References Cited

U.S. PATENT DOCUMENTS

| | | | |
|---|---|---|---|
| 857,662 | 6/1907 | Odor | 283/65 X |
| 4,319,541 | 3/1982 | Sullivan et al. | 283/115 X |
| 4,369,358 | 1/1983 | Adams | 283/65 X |
| 4,580,814 | 4/1986 | Berler | 283/65 X |
| 5,057,067 | 10/1991 | Hibsch | 283/65 X |

Primary Examiner—Willmon Fridie
Attorney, Agent, or Firm—Ralph S. Branscomb

[57] ABSTRACT

A vaccination scheduler is used by health professionals to easily and unequivocally establish the appropriate timing and dosage for vaccinations routinely given to children. The invention clarifies the maze of instructions and caveats that otherwise must be born in mind by the health professional, resulting in much under-vaccination and disease. A sequence of vaccine-specific dials display the needed information in a sequence which indexes with the windows of a front panel to isolate the sequencing and dose information needed for the particular patient.

15 Claims, 6 Drawing Sheets

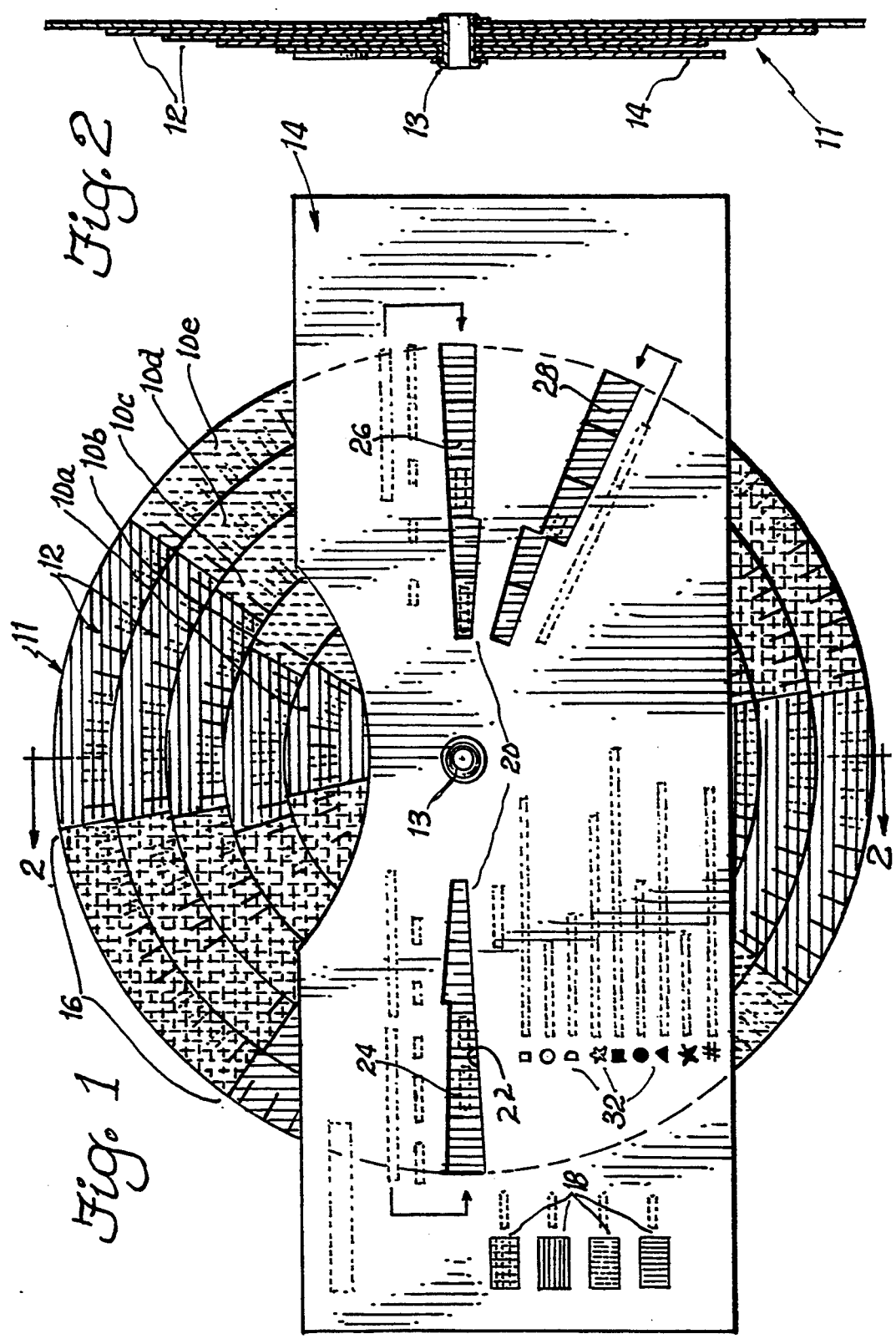

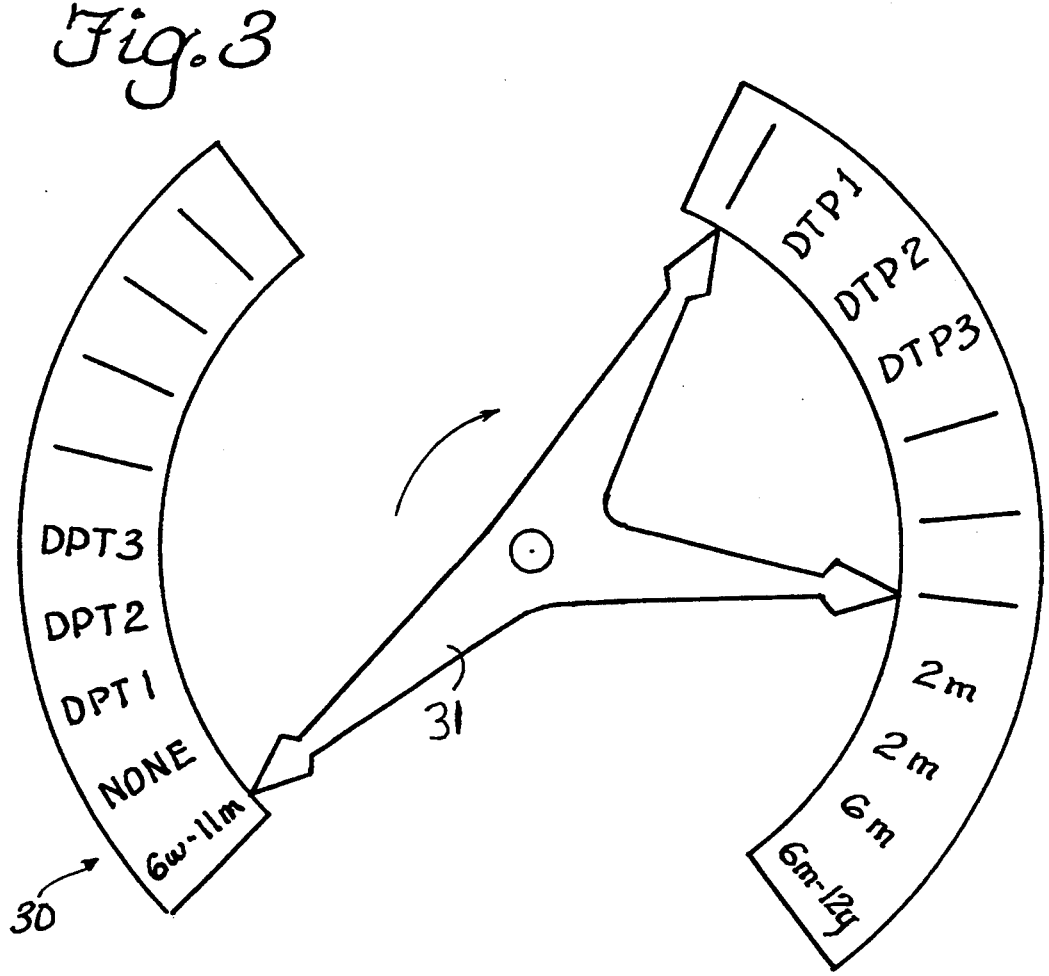

Hib conjugate▲

| Age Group | Prev. Dose 1M or ( ) ago | Vaccine Due | Minimum Return Time or Age (bold) |
|---|---|---|---|
| (6wk-11M) | None | Hib1 | 1M;2M* |
|  | Hib1 | Hib2 | 1M■;2M*■;12M |
|  | Hib2 | Hib3■ | 2M; &12M |
|  | Hib3(2M) | — | 12M |
| (12-14M) |  |  |  |
|  | None | Hib1 | 1M |
|  | Hib1 | Hib2 | 1M |
|  | Hib2 | Hib3 | 2M■ |
|  | Hib3(2M) | Hib4■ | — |
| (15M-6Y) |  |  |  |
|  | None | Hib1 | — |
|  | Hib1# | Hib2 | — |
|  | Hib2 | Hib3● | — |
|  | Hib3(2M) | Hib4■ | — |
| (7-18Y) |  |  |  |
|  | None | Hi-Risk | — |
|  | Hib1 | — | — |
|  | Hib2 | — | — |
|  | Hib3(2M) | — | — |

\* If given on recommended, routine schedules
■ Only if Schedule A (see reverse) and dose 1 given by 6M old
● Only if dose 1 given by 12 M old
▲ Schedules vary by manufacturer; see reverse panel
\# If dose given at > 15M old, no further doses needed

---

Oral Polio Vaccine

| Age Group | Prev. Dose 1M or ( ) ago | Vaccine Due | Minimum Return Time or Age (bold) |
|---|---|---|---|
| (6wk-11M) | None | OPV1 | 6W;2M* |
|  | OPV1(6W) | OPV2 | 6W;2M* |
|  | OPV2(6W) | OPV3 | 4-6Y |
|  | OPV3 | — | 4-6Y |
| (12-14M) |  |  |  |
|  | None | OPV1 | 6W; 2M* |
|  | OPV1(6W) | OPV2 | 6W |
|  | OPV2(6W) | OPV3 | 4-6Y |
|  | OPV3 | — | 4-6Y |
| (15M-6Y) |  |  |  |
|  | None | OPV1 | 6W;2M* |
|  | OPV1(6W) | OPV2 | 6W |
|  | OPV2(6W) | OPV3☆ | 6M; &4-6Y |
|  | OPV3(6M)☆ | OPV4△ | — |
| (7-18Y) |  |  |  |
|  | None | OPV1 | 6W |
|  | OPV1(6W) | OPV2 | 6W;6M* |
|  | OPV2(6W) | OPV3 | — |
|  | OPV3(6M)☆ | OPV4 | — |

\* If given on recommended, routine schedules
☆ If given after 4th birthday, no 4th dose needed
△ Usually given at 4-6Yrs old

*Fig. 5a*

Hepatitis B

| Age Group | Prev. Dose 1M or ( ) ago | Vaccine Due | Minimum Return Time or Age (bold) |
|---|---|---|---|
| (Birth-12M) | None | HepB1★ | 1M; 2M* |
| | HepB1 | HepB2 | 2M;5M*;&4M |
| | HepB2(2M) | HepB3 | — |
| (12-14M) | | | |
| | None | HI-Risk | 1M |
| | HepB1 | HepB2 | 2M or 5M* |
| | HepB2(2M) | HepB3 | — |
| (15M-6Y) | | | |
| | None | HI-Risk | 1M |
| | HepB1 | HepB2 | 2M or 5M* |
| | HepB2(2M) | HepB3 | — |
| (7-18Y) | | | |
| | None | HI-Risk | 1M |
| | HepB1 | HepB2 | 2M or 5M* |
| | HepB2 | HepB3 | — |

* If given on recommended, routine schedules
★ Usually given at birth

Measles, Mumps, Rubella

| Age Group | Prev. Dose 1M or ( ) ago | Vaccine Due | Minimum Return Time or Age (bold) |
|---|---|---|---|
| (6wk-11M) | None | — | 12M |
| (12-14M) | None | MMR1 | 4-6Y |
| | MMR1 | — | 4-6Y |
| (15m-6Yr) | | | |
| | None | MMR1 | 1M;&4-6Y |
| | MMR1 | MMR2△ | — |
| (7-18Yr) | | | |
| | None | MMR1 | 1M |
| | MMr1 | MMR2 | — |

△ Usually given at 4-6 Yrs old

VARICELLA-ZOSTER VIRUS VACCINE

| Age Group | Prev. Dose 1M or ( ) ago | Vaccine Due | Minimum Return Time or Age(bold) |
|---|---|---|---|
| 6W-11M | None | — | 12M |
| 12M-14M | None | VV1 | — |
| 15M-6Y | None | VV1 | — |
| 7-18Y | None | VV1 | 1M+;2M* |
| | VV1 | VV2+ | — |

* If given on recommended, routine schedule
+ If dose 1 given prior to 13th birthday, no second dose needed

*Fig. 5b*

DTP (DT, DTaP, Td)

| Age Group | Prev. Dose 1M or ( ) ago | Vaccine Due | Minimum Return Time or Age (bold) |
|---|---|---|---|
| (6wk-11 mo) | None | DTP1 | 1M or 2M* |
| | DTP1 | DTP2 | 1M OR 2M* |
| | DTP2 | DTP3 | 6M |
| | DTP3(6M) | — | 6M; & 12M |
| (12-14M) | | | |
| | None | DTP1 | 1M |
| | DTP1 | DTP2 | 1M |
| | DTP2 | DTP3 | 6M |
| | DTP3(6M) | DTP4 | 4-6Y |
| | DTP4(6M) | — | 4-6Y |
| (15M-6yr) | | | |
| | None | DTP1 | 1M |
| | DTP1 | DTP2 | 1M |
| | DTP2 | DTP3 | 6M |
| | DTP3(6M) | DTP4o☐ | 6M; & 4-6Y |
| | DTP4(6M)☐ | DTP5o☐ | 10Y |
| (7-18Yr) | | | |
| | None | Td1 | 1M |
| | Td/DTP1 | Td2 | 6M |
| | Td/DTP2(6M) | Td3 | 10Y |
| | Td/DTP(6M) | Td4 | 10Y |

* If given on recommended, routine schedules
o DTaP may be given
△ Usually given @ 4-6Y old
☐ If dose 4 given @ > 4Y old, give booster every 10Y

*Fig. 5c*

VACCINATION SCHEDULER

BACKGROUND OF THE INVENTION

The vaccination of children is age critical, and also critically dependent on proper timing of the doses of the particular vaccine sequence. In the United States there are five immunizations routinely administered to children, some of which are multiple vaccines in one application. Each vaccination sequence must be administered within certain time and age windows or the vaccination may not be effective. The inventor's own child contracted a life-threatening case of the Whooping Cough (pertussis) because of inappropriately administered vaccine.

With all of these sequences, each having a different time sequence and its own number of doses, it is easy for the health professional to become confused, especially if he or she is not in the business of administrating such immunization doses on a routine basis. With a room full of children to inoculate, each having a different immunization history, and each requiring the administration of the next dose of several different vaccinations, the process is time-consuming and it is easy to understand how and even a trained professional will make mistakes.

To further complicate matters, in addition to the recommended timing for delivery of each vaccine, there are medical advisories associated with certain specific combinations of characteristics of age and other factors that must be heeded. Further, the vaccinations that are administered in the United States are not the same as those applied in other countries. Even states in the U.S. vary in their vaccination schedules. When children move from one region to another, or when the health professional is traveling to another health jurisdiction, the incidence of vaccination errors increases.

To clarify dosing schedule differences, improve efficiency, ensure that the appropriate timing is established between doses and to improve decision making accuracy, a job/performance aid is needed in the area of vaccine screening and delivery.

SUMMARY OF THE INVENTION

The instant invention fulfills the above-stated need by providing an immunization sequencer which in one unit contains all of the information the administrator would need to know to administer vaccines accurately to innumerable children on a daily basis. The information is arranged so that it is difficult to make a mistake, even for a trainee in the field, or a tired administrator who has been administering doses for many hours, and would otherwise be at high risk.

The immunization sequencer uses a series of coaxial rotors having peripheral bands which display several groups of indicia which must correlate in any particular case. The inoculation or vaccination administrator needs to know, a) the time that must have lapsed since the last dose if this is not the first dose,
b) which dose to give this time, which depends on (a) above and age, and
c) the time the child must wait, or the age he must achieve, after this dose before coming in for the next dose.

Also, there are certain caveats based primarily on age and vaccine type that must be available to the administrator on a real-time basis so that opportunities are not missed and a child is not left vulnerable to a vaccine-preventable disease.

Each of the coaxially mounted rotors correlates with a different immunization sequence, for example one rotor covers measles, mumps and rubella, another hepatitis B and so forth. Each rotor has eight sectors and represents four age spectra so that each age group is allotted two of the sectors on the rotor. The first sector is indexed with a window on an overlying panel and displays the child's last dose and the time that must have passed since that dose. The other sector allocated to that age group is indexed by another window on the front panel and identifies the current dose that should be administered and the time that must elapse or the age that must be reached before the next administered dose. Exceptions and clarification are noted by symbols and an explanatory legend. In this manner all age groups are covered for the particular disease against which immunization is sought on a single rotor, with another rotor being required for each additional vaccine-preventable disease.

BRIEF DESCRIPTION OF THE DRAWINGS

FIG. 1 is a front elevation view of the 5-rotor embodiment of the sequencer;

FIG. 2 is a section taken along line 2—2 of FIG. 1;

FIG. 3 is a diagram which clarifies the coordination between band sectors;

FIG. 4a is a front elevation view, slightly diagrammatic, illustrating the subsector division scheme of the radially incremented band sequence of the 6 -band modifation of the 5-band embodiment of FIGS. 1 and 2;

FIGS. 5a, 5b and 5c are complete printouts of all the data incorporated into the 5-band embodiment of the invention, providing all the information that the health professional needs to know to apply the five vaccine sequences identified in those figures, up-to-date as of October 1994, the printing date.

DETAILED DESCRIPTION OF THE PREFERRED EMBODIMENT

Figure 4B:
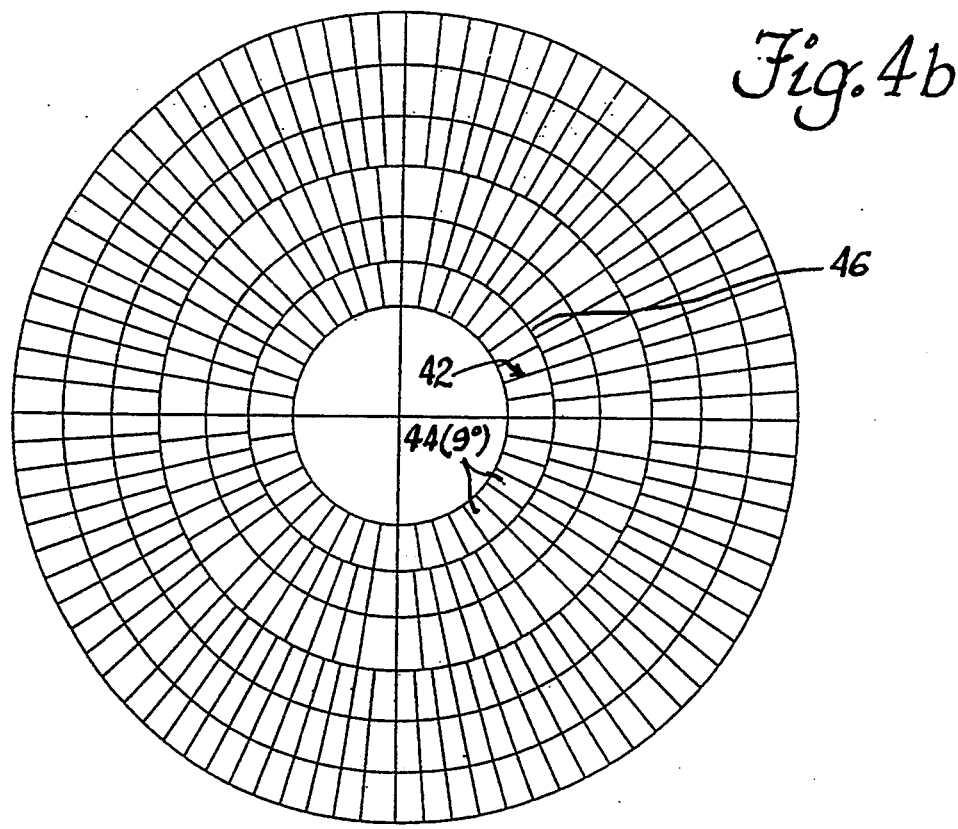
FIG. 4a is a front elevation view, slightly diagrammatic, illustrating the subsector division scheme of the radially incremented band sequence of the 5-band embodiment of FIGS. 1 and 2.

The invention can be implemented in a variety of different ways, with the illustrated embodiment being a rotor cluster comprising a series of rotors 10(a) to 10(e) shown in FIGS. 1 and 2, forming a rotor cluster 11. Each rotor corresponds to a particular vaccine, and each rotor has a diameter greater than the rotor in front of it by an identical amount from rotor to rotor so that a uniformly radiused operative annular band 12 is displayed by each rotor. The pivot point of the rotors, at which they are all fastened together in a stack rotatable about a single axis, is typically established by a rivet 13. The rivet also captures the front panel 14, so that all of the elements are mutually rotatable about the axis defined by the rivet.

Each of the rotors is divided into eight 45-degree sectors 16. As can be visualized from an examination of FIG. 1, the sectors, all being 45° degrees in angular extent, will align so that the combination of the angular sectors visually defines a single sector for the entire circle. Each of these sectors is color-coded for a specific age, there being two sectors on opposite sides of the respective rotor color-coded for the same age, and the ages being identified with the coding on the front panel at 18 as indicated in FIG. 1.

The front panel defines a window system 20 which virtually dictates that the appropriate data from the indicia on the underlying rotor bands is displayed through the windows. The window system of the embodiment illustrated includes a first window 22, which cuts a radial swath 24 across all of the bands and aligns with one of the subsectors of the sectors 16 of each of the rotor bands 12. On the opposite side of the front panel are the second and third windows, indicated at 26 and 28, which similarly align with the subsectors of the rotor bands on the opposite side of the dial from the subsectors seen through the window 22. The arrangement of the x o rotors is such that for a particular color code representing a particular age group, all of the windows would appear in the same color. If the administrator were immunizing a child between the ages of six weeks and 11 months, whose color code is yellow, and pink appeared on one of the bands in any of the windows in the front panel, the administrator would be immediately alerted to the fact that the rotor in question was misaligned and would be prompted to rotate it until yellow appeared in that band to match the others.

A typical sequence for an age group is shown in FIG. 3, which is a diagram illustrating the correlation of the indicia on the two segments of the band pertaining to DTP (diphtheria, tetanus, pertussis) vaccine. These sectors all relate to a child between the age of six weeks and 11 months. This is indicated in the leftmost subsector of the sector identified at 30, which is pointed out by the left rotating arrow of the indicator 31 in FIG. 3, which corresponds to window 22 in the actual unit. The arrows of the indicator 31 in the FIG. 3 diagram are together defined as a single rigid unit so that they move together about the central pivot, directly corresponding to the actual action of the windows 22, 26 and 28 of the front panel, respectively clockwise starting with the left arrow. It can be seen that the other two arrows, on the right side of the figure, point to blank spaces indicated by a continuous slash.

As the rotor is moved counterclockwise, corresponding to the arrows in FIG. 3 moving clockwise, the left arrow first contacts the "NONE", indicating that a child in a six weeks to 11 months age bracket is present who has not had DTP vaccine before. The other two arrows indicate "DTP1" and "2", respectively, indicating that the child is in line for the first dose of the DTP vaccine and should wait 2 months before coming back for the second dose. The left window (22) identifies the previous dose as well as the fact that one month must have elapsed from the prior dose, unless there is some other number in parentheses.

Window 26 has a legend beside it on the front panel which indicates that it is the "dose now due" window, and window 28 is identified with the minimum time that must lapse before the next dose is administered.

Thus the basic unit has indicia divided into three groups for the three windows, identifying:
the last dose, if any;
the appropriate present dose;
the time lapsed since the last dose; and
the return time that must pass or age that must be reached before the next dose.

In addition to this information, a number of special caveats and indications associated with a particular dose and age, for a particular vaccine are printed on the rotor bands and footnoted in a legend on the front panel.

Rather than numerical footnotes, symbols are used as indicated at 32 to simplify visual correlation under hectic conditions. These caveats and notes are listed at the bottom of the indicia listing for the various rotor bands, printed *en toto* in FIGS. 5a, 5b, and 5c.

In order to make the sequencer as small as possible without causing the innermost rotor band to be unreadable, the subsectors of the outer bands and inner bands differ in angular extent. That way, the lettering on the inside bands can be the same size as on the outer bands, there are just fewer subsectors on the inner rotors, which is therefore used for the shorter vaccine sequences.

The subsector division scheme derived by the inventor is shown in FIG. 4. First, it can be seen that when properly aligned all of the 45° annular sectors fall into radial alignment. If the subsectors are to be different-sized, alignment cannot be possible for all of the radially adjacent subdivisions. A circular demarcation line 34 (imaginary) separates the inner two bands from the outer three. The outer three bands are divided into 4° subsectors as indicated at 36. Because four does not divide evenly into 45°, the last subsector in each outer sector, when rotating counterclockwise in FIG. 4, is an adjustment subsector of 5°.

The inner two subsectors, on the other hand, start at the same radial line of departure, but are divided into 6° subsectors as shown at 38. Since six does not divide evenly into 45° either, the last subsector is 9° as indicated at 40.

This particular subsector scheme achieves the minimum subsector misalignment. Most of the subsectors will align every 12° at the interface 34. Referencing the "normal" or non-adjustment sectors, a 12° span corresponds to three of the outer 4° subsectors, and two of the inner 6° subsectors. The last subsectors of the inner and outer groups, which are the adjustment subsectors, align at the 34 interface with two of the outer subsectors (4° plus 5°) spanning the same angle as the single 9° inner subsector, so that overall the misalignment is minimized.

Figure 4A:
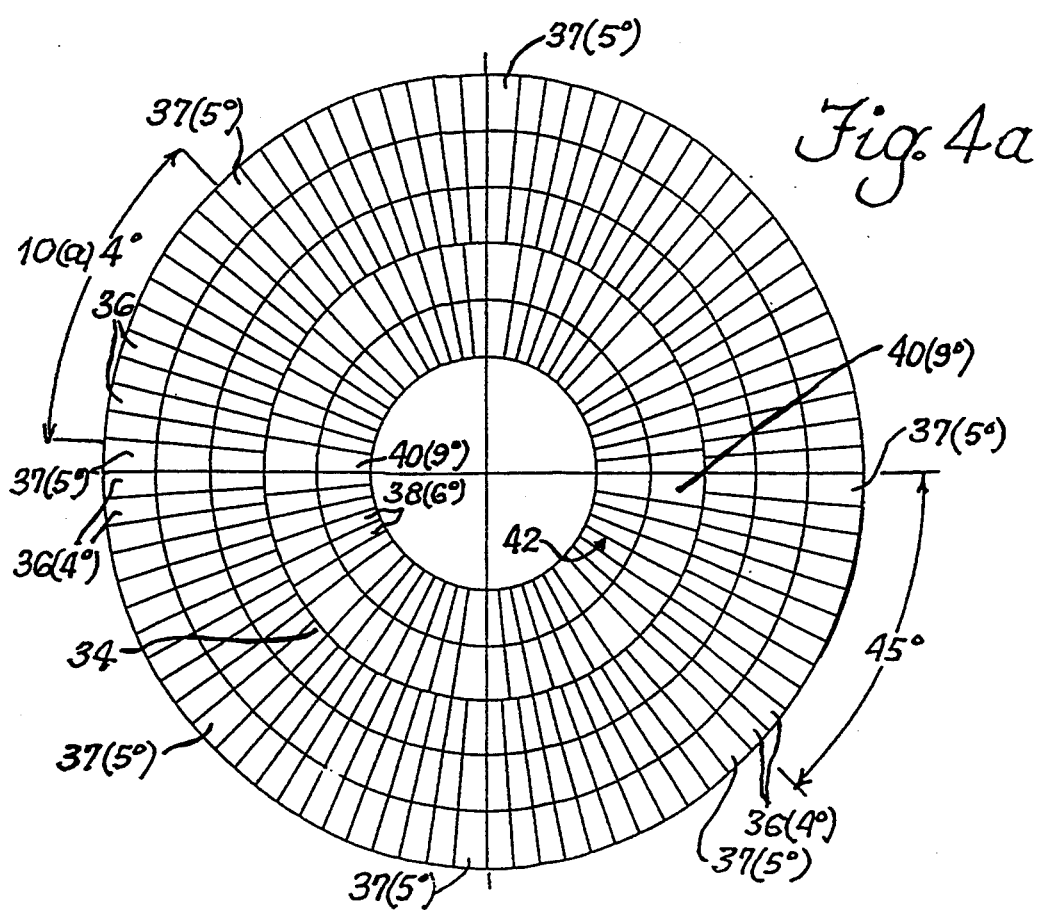

FIG. 4b illustrates a modification in which 6 rotors are used by adding an additional innermost rotor. This rotor does not disturb the configuration of the outer five, but adds eight sectors of 5 uniform 9° subsectors, each two of which align with three of the radially outer 6° subsectors and the single 9° adjustment subsector. The alignment of all the rotors looks like this:

| FIG. 4a: | | | |
|---|---|---|---|
| Outer: | 4°4°4° 4°4°4° | 4°4°4° | 4°5° |
| Inner: | 6°6° 6°6° | 6°6° | 9° |
| FIG. 4b: | | | |
| Inner, re-grouped: | 6°6°6° | 6°6°6° | 9° |
| innermost: | 9°9° | 9°9° | 9° |

The misalignment however, while achieving equality of letter size, causes the windows in the front panel to be jagged as indicated in FIG. 1 in order to span the full range of the subsectors of the various bands.

The vaccination schedule is uniquely flexible in that obviously any sequence of vaccinations can be added or deleted depending on the region or other criteria by adding or deleting one of the rotors. Any rotor can be updated with an applique, or the pivot rivet can be made removable and replacement rotors can be installed, as time passes and vaccination techniqus and information are updated. Rather than having to keep track of numerous newsletter updates for various changes, the vaccine scheduler would be updated on a regular basis so that it is always current, enabling administrators to work with confidence, and parents to relax.

It is hereby claimed:

1. A vaccination sequencer comprising:
   (a) a rotor duster comprised of a stack of parallel interconnected coaxially journalled rotors defining a common journal and having diameters which respectively increment from the front to the back of said cluster such that a peripheral annular band of each rotor extends radially beyond any forward rotors to be frontally visible, said bands having substantially uniform annular radial thicknesses from one to another;
   (b) each of said rotors being correlated with a particular type of immunization sequence comprising the structured administration of a series of time-spaced doses related to one or more particular diseases and defining on the respective band an indicia array comprised of a plurality of angularly spaced indicia elements correlated with said particular type of immunization sequence;
   (c) a front panel rotatably mounted to said cluster to permit mutual rotation about said common journal and defining a window system which selectively indexes with selected indicia selected from said plurality of indicia elements on each band as the respective rotor is rotated relative to said from panel to reveal said selected indicia while masking indicia elements adjacent said selected indicia;
   (d) said window system spanning all of said bands and defining identifiers adjacent the respective bands identifying the immunization type to which the band pertains;
   (e) the indicia array of each band being arranged as groups including a present dose indicia group identifying a particular dose in the particular type of immunization sequence correlated with the respective rotor, and a time lapse indicia group indicating the time that should have elapsed since the prior dose was administered, and a return time indicia group indicating the interval that should elapse between said particular dose and the return visit for any subsequent dose; and,
   (f) said window system and the indicia array on each of said rotors being geometrically correlated such that correlated present dose, time lapse and return time indicia are simultaneously visible for any selected dose, providing the health provider with all the sequencing information necessary to decide the appropriateness of a particular dose and the appropriate time and age to administer any subsequent dose in the selected immunization sequence.

2. Structure according to claim 1 wherein said window system comprises at least two windows.

3. Structure according to claim 2 wherein the array of indicia on each band is arranged such that as one window indexes with said present dose indicia another of said windows indexes with said return time indicia.

4. Structure according to claim 3 wherein said indicia arrays each includes a next dose indicia group identifying the next dose to be taken in the respective immunization sequence, and said windows simultaneously index with correlated indicia from said present dose, time lapse, return time and age, and next dose indicia groups.

5. Structure according to claim 4 wherein said window system comprises three windows and said lapse and present dose indicia groups are geometrically linked to be together viewed through a single one of said windows and said next dose and return time indicia groups are revealed through the other two of said windows, respectively.

6. Structure according to claim 5 wherein said windows are elongated and substantially radially extended and the indicia of corresponding indicia groups from different bands are of substantially uniform font size such that radially inner indica elements occupy a greater angular span than radially outer indicia elements, and said windows define lateral discontinuities to accommodate abrupt radian differentials between radially adjacent indicia arrays on respective adjacent bands.

7. Structure according to claim 1 wherein each of said arrays is defined as a substantially continuous annular array around the respective band, and is subdivided into sectors by age with color coding so that a particular sector of each band defined in a particular color displays said present dose indicia correlated with a particular age spectrum and said lapse and return time indicia groups associated with the respective present dose group likewise correlate in color and age appropriateness to same.

8. Structure according to claim 7 wherein said annular arrays are each subdivided into four color-code age spectra.

9. Structure according to claim 8 wherein said bands are subdivided into said indicia groups and color-coded in 45-degree sectors for eight total sectors, two for each age spectrum, and said window system includes two separate windows for indexing with each of said two sectors for each age spectrum.

10. Structure according to claim 9 wherein said indicia arrays each include next dose indicia groups and said two sectors for each age spectrum display include said present dose and lapse time indicia groups in one of said two sectors and said next dose and return time indicia groups in the other of said two sectors, and said two windows index with said respective two sectors and their respective groups.

11. Structure according to claim 1 wherein said bands are logically divided in to angularly consecutive radian subsectors for displaying indicia elements, and at least two different division schemes are used for different bands such that an inner and an outer group of bands are defined such that the inner band has fewer subsectors, but of greater radial extent, than an outer group of bands.

12. Structure according to claim 11 wherein the subsectors of said inner and outer band groups have radial perimeters which align every 45 degrees such that said sectors of the bands are of the same angular extent despite the dissimilarity between the radian measurement of the subsectors.

13. Structure according to claim 11 wherein the sectors of said band groups are subdivided into subsectors such that when progressing in one angular direction each consecutive three subsectors of said outer band group are alignable with each consecutive two of the subsectors of said inner group except for an adjustment subsector defining as the last subsector of each sector.

14. Structure according to claim 13 wherein the subsectors of said outer group are 4° wide except for the adjustment subsector which is 5° wide, and the subsectors of said inner group are 6° wide with a 9° wide adjustment subsector.

15. Structure according to claim 11 wherein said bands include an innermost band radially inward of said inner group and having subsectors substantially uniformly 9° in angular extent to define five angularly contiguous uniform subsectors per sector.

* * * * *